United States Patent [19]

Tsaklakidis et al.

[11] Patent Number: 5,683,994
[45] Date of Patent: Nov. 4, 1997

[54] PHOSPHOSUCCINIC ACID DERIVATIVES, PROCESSES FOR THE PRODUCTION THEREOF AND PHARMACEUTICAL AGENTS CONTAINING THESE COMPOUNDS

[75] Inventors: Christos Tsaklakidis, Weinheim; Angelika Esswein, Singen; Gerd Zimmermann, Mannheim; Frieder Bauss, Lambsheim, all of Germany

[73] Assignee: Boehringer Mannheim GmbH, Mannheim, Germany

[21] Appl. No.: 553,556

[22] PCT Filed: Jun. 17, 1994

[86] PCT No.: PCT/EP94/01980

§ 371 Date: Dec. 18, 1995

§ 102(e) Date: Dec. 18, 1995

[87] PCT Pub. No.: WO95/00522

PCT Pub. Date: Jan. 5, 1995

[30] Foreign Application Priority Data

Jun. 18, 1993 [DE] Germany ............... 43 20 223.3

[51] Int. Cl.$^6$ ............... A61K 31/66; A61K 31/19; C07C 55/10

[52] U.S. Cl. ............... 514/121; 562/24
[58] Field of Search ............... 514/121; 562/24

[56] References Cited

FOREIGN PATENT DOCUMENTS

| 2360797 | 6/1975 | Germany. |
| 9312122 | 6/1993 | WIPO. |
| 9324131 | 12/1993 | WIPO. |

*Primary Examiner*—Jacqueline Haley
*Attorney, Agent, or Firm*—Nikaido Marmelstein Murray & Oram LLP

[57] ABSTRACT

Compounds of formula I are disclosed,

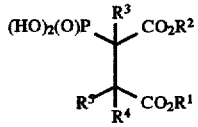

as well as processes for their production and pharmaceutical agents containing these compounds suitable for treating disorders of calcium metabolism.

20 Claims, No Drawings

PHOSPHOSUCCINIC ACID DERIVATIVES, PROCESSES FOR THE PRODUCTION THEREOF AND PHARMACEUTICAL AGENTS CONTAINING THESE COMPOUNDS

This is a National Stage application of PCT/EP94/09180 filed Jun. 17, 1994 and published as WO 95/00522 on Jan. 5, 1995

The present invention concerns new phosphonosuccinic acid derivatives, processes for the production thereof as well as pharmaceutical agents containing these substances.

It has been found that phosphonosuccinic acid derivatives of the present invention exhibit an excellent action on calcium metabolism and thus are suitable for treating disturbances of calcium metabolism. They can above all be used when bone formation and bone degradation are disturbed, i.e. they are suitable for treating diseases of the skeletal system such as e.g. osteoporosis, Morbus Paget, Morbus Bechterew and others.

Due to these properties they can also be used in urolithiasis therapy and for the prevention of heterotopic ossification. Furthermore they form the basis for treating rheumatoid arthritis, osteoarthritis and degenerative arthrosis through their influence on calcium metabolism.

The present invention concerns compounds of the general formula I,

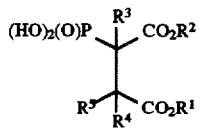

in which $R^1$, $R^2$ can be, independently of each other hydrogen, lower alkyl, cycloalkyl or arylmethyl, $R^3$, $R^4$ can be, independently of each other, hydrogen, lower alkyl or one of the groups $OR^6$ or $NR^7R^8$ or, together with the atoms to which they are bound, can form a five- to seven-membered carbocyclic ring or a heterocyclic ring containing one to two heteroatoms, $R^5$ denotes lower alkenyl, cycloalkyl, cycloalkenyl, monocyclic arylalkyl, bicyclic aryl, biaryl or a group of formulae a) or b) or, together with $R^4$ and the carbon atom to which it is bound, forms a five- to seven-membered carbocyclic or heterocyclic ring which can be substituted if desired, a) $R^9$—X-alk-

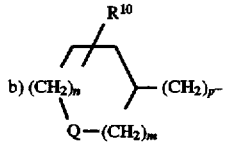

$R^6$ denotes hydrogen, lower alkyl or arylmethyl, $R^7$, $R^8$ denote, independently of each other, hydrogen or lower alkyl or, together with the nitrogen atom to which they are bound, form a five- to six-membered heterocyclic ring, $R^9$ denotes hydrogen, lower alkyl, lower alkenyl, cycloalkyl, cycloalkenyl, monocyclic or bicyclic aryl, biaryl, $R^{10}$ denotes a group of formula a), X denotes a valency dash, oxygen or sulphur, Q denotes oxygen, sulphur or nitrogen, alk denotes a valency dash, a methylene chain, a saturated or unsaturated alkylene chain with 2–6 carbon atoms, n=0–3 m=0–2 and p=0–5 as well as pharmacologically acceptable salts thereof and optical isomers wherein in the case that $R^3$ denotes hydrogen or $C_1$–$C_3$ alkyl and $R^4$ denotes hydrogen, $R^5$ may not be hydrogen, hydroxy, methoxy, $c_1$–$C_3$ alkyl or aryl, and in the case that X denotes oxygen or sulphur and $R^4$ denotes one of the groups $OR^6$ or $NR^7R^8$ alk may not be a valency dash.

Phosphonosuccinic acid derivatives of formula I have already been described in DE-A-23 60 797 in which $R^3$ denotes hydrogen or $C_1$–$C_3$ alkyl, $R^4$ denotes hydrogen and $R^5$ denotes hydrogen or $C_1$–$C_3$ alkyl for influencing the deposition and dissolution of sparingly soluble calcium salts.

Additional compounds of formula I are described in the following chemical abstracts without information on a possible use as pharmaceutical agents:

Compounds in which $R_3$=H or $CH_3$; $R^4$=H and $R^5$=$OCH_3$ in CA, 105(5):42932x and CA, 104(1):5939.

Compounds in which $R^3$=H; $R^4$=H and $R^5$=phenyl which may be substituted in CA 115(23):255757 n and CA106 (21):176504 p.

Lower alkyl should in all cases denote a straight-chained or branched $C_1$–$C_6$ alkyl group such as methyl, ethyl, propyl, isopropyl, butyl, isobutyl, pentyl or hexyl, in particular methyl, ethyl, propyl, isobutyl and pentyl.

Lower alkenyl denotes unsaturated residues with 3–6 carbon atoms such as e.g. allyl, but-2-enyl, hexy-2,4-dienyl, above all allyl.

Cycloalkyl denotes a 3–7-membered ring which may be substituted if desired such as a cyclopropyl, cyclobutyl, cyclopentyl, cyclohexyl or cycloheptyl ring, in particular a cyclopropyl, cyclopentyl and cyclohexyl ring. These cycloalkyl residues can be substituted once or twice by $C_1$–$C_6$ alkyl groups, preferably a methyl, ethyl or isopropyl group as well as by hydroxy, methoxy, benzyloxy, amino, methylamino, dimethylamino, benzylamino groups or by chlorine or bromine.

Cycloalkenyl denotes a cyclopentenyl, cyclohexenyl or cycloheptenyl ring which may be substituted if desired. These rings can be substituted once or twice by a $C_1$–$C_6$ alkyl group preferably a methyl, ethyl or isopropyl group as well as by chlorine, bromine or hydroxy, methoxy, benzyloxy, amino, methylamino, dimethylamino or benzylamino groups.

If the residues $R^3$ and $R^4$ together with the carbon atoms to which they are bound form a carbocyclic or heterocyclic ring, this is a saturated or unsaturated 5–7-membered ring such as a cyclopentyl, cyclohexyl, cycloheptyl, pyrrolidine, piperidine, azepine, tetrahydrofuran, tetrahydropyran, morpholine, dioxane, cyclopentenyl, cyclohexenyl, pyrroline, dihydrofuran or a dihydropyran ring in particular a cyclopentyl, cyclohexyl, tetrahydrofuran, morpholine, cyclohexenyl or a dihydropyran ring.

If $R^4$ and $R^5$ together with the carbon atoms to which they are bound form a carbocyclic or heterocyclic ring, this is a saturated or unsaturated 5–7-membered ring such as a cyclopentyl, cyclohexyl, cycloheptyl, pyrrolidine, piperidine, azepine, tetrahydrofuran, tetrahydropyran, morpholine, dioxane, cyclopentenyl, cyclohexenyl, pyrroline, dihydrofuran or dihydropyran ring in particular a cyclopentyl, cyclohexyl, cyclohexenyl, pyrrolidine, piperidine, tetrahydrofuran, tetrahydropyran or morpholine ring.

The carbocyclic and heterocyclic rings can if desired be substituted once or twice by $C_1$–$C_6$ alkyl groups, preferably a methyl, ethyl or isopropyl group as well as by chlorine, bromine or hydroxy, methoxy, benzyloxy, amino, methylamino, dimethylamino or benzylamino groups.

Aryl usually denotes a phenyl residue which can be substituted once or several times if desired.

Bicyclic aryl usually denotes an indan, naphthalene or anthracene residue which can be substituted once or several times if desired and preferably denotes a naphthalene residue.

Biaryl usually denotes a biphenyl residue which can be substituted once or several times if desired.

Aryl, bicyclic aryl and biaryl residues can if desired be substituted once or several times by $C_1$–$C_6$ alkyl groups, preferably a methyl, ethyl or isopropyl group as well as by chlorine, bromine, fluorine or hydroxy, alkoxy such as e.g. methoxy, benzyloxy, acetyloxy, carboxy, ethoxycarbonyl, aminocarbonyl, methylaminocarbonyl, dimethylaminocarbonyl, cyano, amino, methylamino, dimethylamino, benzylamino, acetylamino, benzoylamino and amidino groups.

Arylalkyl usually denotes an unsubstituted or once or several fold substituted benzyl, phenethyl, phenylpropyl, phenylbutyl or phenylpentyl residue preferably a benzyl, phenethyl, or phenylpentyl residue. $C_1$–$C_6$ alkyl residues come into consideration as substituents, preferably methyl, ethyl or isopropyl as well as chlorine, bromine, fluorine or hydroxy, methoxy, benzyloxy, acetyloxy, carboxy, ethoxycarbonyl, aminocarbonyl, methylaminocarbonyl, dimethylaminocarbonyl, cyano, amino, methylamino, dimethylamino, benzylamino, acetylamino, benzoylamino and amidino groups.

When alk is a saturated or unsaturated, straight-chained or branched alkylene chain, it represents residues such as e.g. methylene, ethylene, propylene, butylene, 2-methyl-propylene, pentylene, 1,1-dimethylpropylene, 2,3-dimethylpropylene, 2,2-dimethylpropylene, 2-methylbutylene, hexylene, 2,3-dimethylbutylene, 2-methylpentylene, 2-butenylene, 2-butinylene, in particular methylene, ethylene, propylene, butylene, 2-methylpropylene, pentylene, hexylene and 2-butenylene.

Compounds of the general formula I contain at least two asymmetrical carbon atoms, thus optically active compounds of the general formula I are also a subject matter of the present application.

Compounds of the general formula I are prepared according to known processes by saponification from phosphonosuccinic acid esters of the general formula II,

(II)

in which $R^1$, $R^2$, $R^3$, $R^4$, $R^5$ have the above-mentioned meanings and $R^{11}$ denotes a methyl, ethyl or benzyl residue.

Compounds of the general formula II are prepared according to known processes, preferably by reacting a) carboxylic acid derivatives of the general formula III,

(III)

in which $R^4$, $R^5$ and $R^1$ have the above-mentioned meanings and Y denotes a leaving group such as Hal or O—$SO_2$—Z in which Hal should be chloride, bromide or iodide and Z should be methyl, phenyl, p-methylphenyl phenyl or p-nitrophenyl with a phosphonoacetic acid ester of the general formula IV,

(IV)

in which $R^2$, $R^3$ and $R^{11}$ have the above-mentioned meanings, wherein in the case that $R^5$ in compounds of the general formula III denotes a free hydroxyl group, this has to be present in a protected form such as an acyloxy, trialkylsilyloxy or benzyloxy group and if desired the esters that are formed are partially or completely saponified to form the corresponding acids of the general formula I or in the case that $R^4$ denotes hydrogen b) compounds of the general formula V

(V)

in which $R^5$, $R^1$, $R^2$ and $R^3$ have the above-mentioned meanings are reacted with a dialkylphosphite of the general formula VI,

(vi)

in which $R^{11}$ has the above-mentioned meanings and if desired, the esters that are formed are partially or completely saponified to form the corresponding acids or in the case that $R^3$=$R^4$=H c) a compound of the general formula VII

(VII)

in which $R^1$, $R^2$ and $R^{11}$ have the above-mentioned meanings is reacted in a known manner with a compound of the general formula VIII

(VIII)

in which $R^5$ has the above-mentioned meanings and M denotes hydrogen or an alkali metal or alkaline-earth metal and if desired the esters that are formed are partially or completely saponified to form the corresponding acids of the general formula I and if desired they are converted into pharmacologically tolerated salts, d) a compound of the general formula IX

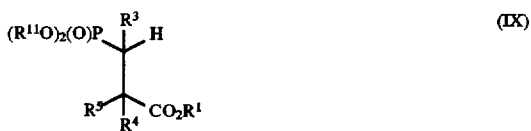

in which $R^1$, $R^3$, $R^4$, $R^5$ and $R^{11}$ have the above-mentioned meanings is reacted successively with a base and a chlorocarbonic acid ester of the general formula X

in which $R^2$ has the above-mentioned meanings or e) a compound of the general formula XI

in which $R^1$, $R^2$, $R^3$, $R^4$ and $R^5$ have the above-mentioned meanings is reacted successively with a base and a compound of the general formula XII $$ClP(O)(OR^{11})_2 \quad (XII)$$

in which $R^{11}$ has the above-mentioned meaning.

Compounds of the general formula I in which $R^3$ is hydrogen and which are prepared according to the processes c) - e) can be converted if desired, into other compounds of the general formula I by treating them with a base and subsequently with a compound of the general formula XIII $$R^3\text{—}Y \quad (XIII)$$

in which $R^3$ and Y have the above-mentioned meanings.

f) Compounds of the general formula I in which $R^3$ and $R^4$ together with the carbon atoms to which they are bound form a ring, can be obtained by reacting Compounds of the general formula XIV or XV

in which $R^1$, $R^2$, $R^3$, $R^4$, $R^5$, $R^{11}$ and Y have the above-mentioned meanings, with a base.

Compounds of the general formula III are prepared in such a way that in the case that Y=Hal a compound of the general formula XVI $$R^5\text{—CHR}^4\text{CO}_2R^1 \quad (XVI)$$

in which $R^1$, $R^4$ and $R^5$ have the above-mentioned meanings is halogenated according to processes known from the literature or in the case that Y in formula III denotes an O—SO$_2$—Z group, the hydroxyl group of a compound of the general formula XVII

in which $R^1$, $R^4$ and $R^5$ have the above-mentioned meanings is converted into the corresponding sulfonic acid ester.

Some of the compounds of the general formula IV are commercially available (Aldrich-Chemie GmbH u. Co. KG) and in special cases are prepared according to known processes by reacting a halogen acetic acid derivative of the general formula XVIII

in which Hal, $R^1$ and $R^5$ have the above-mentioned meanings with a triphosphite of the general formula XIX $$P(OR^{11})_3 \quad (XIX)$$

in which $R^{11}$ has the above-mentioned meanings.

Compounds of the general formula V are prepared by dehydrating a compound of the general formula XX according to known processes

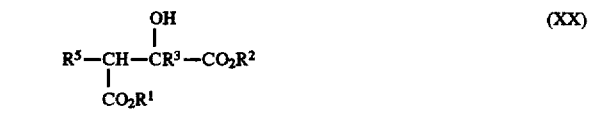

in which $R^1$, $R^2$, $R^3$ and $R^5$ have the above-mentioned meanings.

Compounds of the general formula VI are commercially available (Aldrich Co.).

Compounds of the general formula VII are prepared in a well-known manner by reacting a compound of the general formula XXI

in which $R^1$ and $R^2$ have the above-mentioned meanings, with a compound of the general formula XIX.

If M does not denote hydrogen, compounds of the general formula VIII are metallized according to literature methods. Compounds of the general formula IX are obtained according to known methods by alkylating a compound of the general formula XXII

in which $R^1$, $R^4$ and $R^5$ have the above-mentioned meanings, with a compound of the general formula XXIII $$Hal\text{—}CH_2\text{—}P(O)(OR^{11})_2 \quad (XXIII)$$

in which Hal and $R^{11}$ have the above-mentioned meanings.

Chlorocarboxylic acid esters of the general formula X can be obtained commercially (Aldrich Co.).

Succinic acid derivatives of the general formula XI are prepared by known methods by alkylating a compound of the general formula XXII with a haloacetic acid ester of the general formula XXIV $$Hal\text{—}CH_2\text{—}CO_2R_2 \quad (XXIV)$$

in which Hal and $R^2$ have the above mentioned meanings.

Compounds of the general formula XII can be obtained commercially (Aldrich Co.).

If Y=Hal, compounds of the general formula XIII can be obtained commercially; if Y denotes an O—$SO_2$—Z group, the hydroxyl group of alcohols which are commercially available of the general formula XXV $$R^3\text{—OH} \qquad\qquad (XXV)$$

in which $R^3$ has the meanings stated above, is converted into the corresponding sulfonic acid ester.

Compounds of the general formula XIV or XV are prepared by converting the hydroxyl group of a compound of the general formula XXVI or XXVII

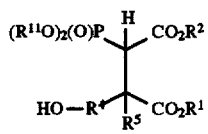

(XXVI)

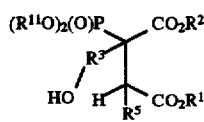

(XXVII)

in which $R^1$, $R^2$, $R^3$, $R^4$, $R^5$ and $R^{11}$ have the meanings stated above, into a halogen or sulfonic acid ester according to known methods. Carboxylic acid esters of the general formula XVI are obtained according to known methods by alkylating a carboxylic acid ester of the general formula XXVIII $$R^5\text{—}CH_2\text{—}CO_2R_1 \qquad\qquad (XXVIII)$$

in which $R^1$ and $R^5$ have the meanings stated above.

Compounds of the general formula XVII can be obtained according to literature methods by oxidizing the appropriate compounds of the general formula XVI.

Compounds of the general formula XVIII are halogenated according to methods known from the literature.

Compounds of the general formula XX are prepared in a known manner by reacting a compound of the general formula XXVIII with a compound of the general formula XXIX

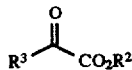

(XXIX)

in which $R^2$ and $R^3$ have the meanings stated above.

Compounds of the general formula XXI are obtained according to known methods by allylic bromination of a compound of the general formula XXX $$\underset{\underset{CO_2R^1}{|}}{CH_3\text{—}C}=CH\text{—}CO_2R^2 \qquad\qquad (XXX)$$

in which $R^1$ and $R^2$ have the meanings stated above.

Compounds of the general formula XXVI are prepared by alkylating a compound of the general formula IV, in which $R^3$ denotes hydrogen, with a compound of the general formula XXXI

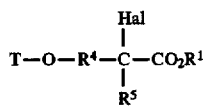

(XXXI)

in which Hal, $R^1$, $R^4$ and $R^5$ have the meanings stated above and T denotes a hydroxy-protecting group such as a benzyl, trimethylsilyl or tert.-butyldimethylsilyl group and the protective group T is removed from the reaction product according to methods known from the literature.

Compounds of the general formula XXVII can be obtained by alkylating a compound of the general formula XXXII

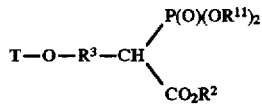

(XXXII)

in which $R^2$, $R^3$, $R^{11}$ and T have the meanings stated above, with a compound of the general formula XVIII and subsequently removing the protective group T.

Compounds of the general formula XXXI can be obtained according to known methods by halogenating a compound of the general formula XXXIII

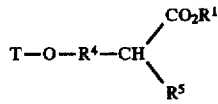

(XXXIII)

in which $R^1$, $R^4$, $R^5$ and T have the meanings stated above.

Compounds of the general formula XXXII are prepared by alkylating a compound of the general formula IV, in which $R^3$ denotes hydrogen, with a compound of the general formula XXXIV $$T\text{—}O\text{—}R^3\text{—}Y \qquad\qquad (XXXIV)$$

in which $R^3$, T and Y have the meanings stated above.

A compound of the general formula XVI or of formula XXXIII is halogenated by reacting it with molecular halogen (chlorine, bromine, iodine), preferably bromine, without a solvent or in an inert solvent such as methylene chloride, chloroform or carbon tetrachloride, preferably carbon tetrachloride, and with addition of red phosphorus, phosphorus trichloride or phosphorus tribromide and at a temperature between room temperature and 100° C., preferably at 90° C. (K. Stoh, Chem. Pharm. Bull. 34, 2078 (1986); H. J. Ziegler, Synthesis 1969, 39). In addition compounds of the general formula XVI can be halogenated by metallizing them in an aprotic solvent such as tetrahydrofuran and at a low temperature, preferably −78° C., with a lithium amid such as lithium diisopropylamide and subsequently reacting the compounds of the general formula XVI that are metallized in the "a" position with bromine, iodine, carbon tetrachloride or carbon tetrabromide (M. Hesse, Helv. Chim. Acta 72, 847 (1989) R. T. Arnold, J. Org. Chem. 43, 3687 (1978)) or with N-chlorosuccinimide or N-bromosuccinimide (W. Oppolzer, Tetrahedron Lett. 26, 5037 (1985)).

Conversion of the hydroxyl group of a compound of the general formulae XVII, XXV, XXVI or XXVII into a sulfonic acid ester is carried out according to usual methods such as for example by condensation with a sulfonic acid chloride such as methane-, benzene-, p-toluene- or p-nitrobenzenesulfonic acid chloride, preferably methane- or p-toluenesulfonic acid chloride in an inert solvent such as methylene chloride, tetrahydrofuran or diethyl ether, preferably methylene chloride, using an auxiliary base such as trimethylamino or triethylamine or pyridine, preferably triethylamine, and at a temperature between 0° C. and room temperature.

The reaction of a compound of formula III with a compound of formula IV, or of a compound of formula IX with a compound of the formula X, or of a compound of formula XI with a compound of formula XII, or the alkylation of a compound of formula XXII with a compound of formula XXIII or of formula XXIV, or the alkylation of a compound of formula IV with a compound of formula XXXI, or of a compound of formula XXXII with a compound of formula XVIII, or cyclization of compounds of the general formula XIV or XV is usually carried out in an aprotic solvent such as toluene, tetrahydrofuran, diethyl ether or dimethylformamide, preferably dimethylformamide or tetrahydrofuran while using a strong base such as potassium hydride, sodium hydride, lithium diisopropylamide or lithium hexamethyldisilylamide, preferably sodium hydride or lithium diisopropylamide, at temperatures between −78° C. and 90° C., but preferably between −10° C. and room temperature.

The reaction of a compound of the general formula V with a compound of the general formula VI is carried out under the conditions of a Michael addition in a solvent such as methanol, ethanol, toluene, tetrahydrofuran or dimethylformamide, preferably methanol, tetrahydrofuran or dimethylformamide, without further additives or using a base such as sodium or potassium methylate or ethylate, sodium hydride, potassium hydride or lithium diisopropylamide, preferably sodium methylate, sodium hydride or lithium diisopropylamide at temperatures between −78° C. and 90° C., but preferably between −10° C. and room temperature.

The reaction of a compound of the general formula VII with a compound of the general formula VIII is usually carried out under the conditions of a Michael addition in a solvent such as methanol, ethanol, toluene, tetrahydrofuran, diethyl ether or dimethylformamide, preferably methanol, tetrahydrofuran or dimethylformamide, without further additives or using a base such as sodium hydride, potassium hydride, lithium diisopropylamide, butyllithium, ethylmagnesium bromide and if necessary a copper salt such as copper chloride or copper bromide to form the respective cuprate of a compound of the general formula VIII (cf. G. H. Posner, Tetrahedron Letters 37, 3215 (1977)) and at temperatures between −78° C. and 90° C., preferably between −78° C. and room temperature.

A compound of the general formula XVIII is usually reacted with a compound of the general formula XIX without a solvent at temperatures between room temperature and 150° C., preferably at 130° C. having a reaction period between 30 minutes and 30 hours, preferably 18 hours.

A compound of the general formula XX is usually dehydrated in a solvent such as benzene, toluene, xylene, chloroform or methylene chloride, preferably toluene or methylene chloride, with addition of a dehydrating agent such as sulphuric acid, phosphoric acid, p-toluenesulfonic acid, preferably p-toluenesulfonic acid, at a temperature between room temperature and the reflux temperature of the solvent used, preferably at 100° C.

A compound XIX is usually reacted with a compound XXI without a solvent at temperatures between 50° C. and 180° C., preferably at 150° C.

The condensation of a carboxylic acid ester of the general formula XXVIII with a ketone of formula XXIX is usually carried out in a solvent such as methanol, ethanol, tetrahydrofuran, diethyl ester or dimethylformamide, preferably methanol or tetrahydrofuran, in the presence of a basic condensation agent such as sodium methylate or sodium ethylate, potassium tert.-butylate, sodium hydride or lithium diisopropylamide, preferably sodium methylate, potassium tert.-butylate or lithium diisopropylamide, at temperatures between −78° C. and 60° C., preferably between −78° C. and room temperature.

For the allylic bromination of 2-methylfumaric acid or maleic acid and derivatives thereof see J. Org. Chem. 34, 1228 (1969). The oxidation of a compound of the general formula XVI to a compound of the general formula XVII is usually carried out in a solvent such as tetrahydrofuran by adding a base such as lithium diisopropylamide or lithium-N-isopropyl-N-cyclohexylamine using an oxidizing agent such as an oxaziridine derivative, molybdenum peroxide or atmospheric oxygen and at temperatures between −78° C. and room temperature, preferably at 50° C. (C. Tamm. Tetrahedron Lett. 26, 203 (1985); F. A. Davis I. Org. Chem. 51, 2402 (1986); C. Winotai Synth. Commun. 18, 2141 (1988)).

Hydrolysis of a phosphonic acid ester group in a compound of the general formula II to the corresponding free phosphonic acid group is usually achieved without a solvent or in an inert solvent such as methylene chloride by means of a trimethylsilylhalogenide such as trimethylsilylbromide or trimethylsilyliodide at a temperature between −50° C. and room temperature, preferably at 0° C.

A carboxylic acid ester group in compounds of the general formulae I or II is saponified according to the usual methods by treating a carboxylic acid ester of the general formula I or II in water or in mixtures of water, tetrahydrofuran, dioxane, methanol or ethanol, preferably in a mixture of water/tetrahydrofuran, with a hydroxide such as sodium, potassium or lithium hydroxide, preferably sodium hydroxide or lithium hydroxide, at temperatures between room temperature and 80° C., preferably at room temperature.

The protecting group of a hydroxyl group in compounds of the general formulae III or XXXI can be removed by treating a compound of the general formula III or XXXI with aqueous mineral acids or mineral bases such as hydrochloric acid or sulphuric acid or sodium hydroxide solution or potassium hydroxide solution or by reacting it with a fluoride such as aqueous hydrofluoric acid or tetrabutylammonium fluoride or subjecting it to a catalytic hydrogenation such as for example with palladium/carbon/hydrogen.

Pure enantiomers of compounds of formula I can be obtained by racemate resolution (by formation of salts using optically active acids or bases) or by using optically active starting materials in the synthesis.

In addition phosphonic and carboxylic acid ester groups in compounds of the general formula I or II can also be saponified by boiling with hydrochloric acid or hydrobromic acid. If benzyl esters are present in compounds of the general formula I or II they can be converted hydrogenolytically into the corresponding free phosphonic or carboxylic acids.

Mono or dialkali or ammonium salts are used above all as pharmacologically tolerated salts which are produced in the usual manner for example by titrating the compounds with inorganic or organic bases such as for example sodium or potassium bicarbonate, sodium hydroxide solution or potassium hydroxide solution, aqueous ammonia or amines such as e.g. trimethylamino or triethylamine. The salts are usually purified by precipitation from water/acetone.

The new substances of formula I according to the invention and salts thereof can be administered enterally or parenterally in a liquid or solid form. All the usual forms of administration come into consideration for this such as tablets, capsules, coated tablets, syrups, solutions, suspensions etc. Water is preferably used as an injection medium which contains the usual additives for injection solutions such as stabilizing agents, solubilizers and buffers.

Such additives are for example tartrate and citrate buffer, ethanol, complexing agents (such as ethylenediaminetetraacetic acid and its non-toxic salts), high-molecular polymers (such as liquid polyethylene oxide) to regulate viscosity.

Liquid carrier substances for injection solutions have to be sterile and are preferably dispensed into ampoules. Solid carriers are for example starch, lactose, mannitol, methylcellulose, talcum, highly dispersed silicic acids, higher molecular fatty acids (such as stearic acid), gelatin, agaragar, calcium phosphate, magnesium stearate, animal or vegetable fats, solid high-molecular polymers (such as polyethylene glycols); preparations which are suitable for oral application can if desired, contain flavourings and sweeteners.

The dose can depend on various factors such as means of administration, species, age and/or individual condition. The daily doses to be administered are about 10–1000 mg/human, preferably 100–500 mg/human and can be taken in one or several doses.

In addition to the compounds mentioned in the examples and compounds which are derived by combining all meanings of substituents stated in the claims, the following succinic acid derivatives as well as their sodium and potassium salts, methyl, ethyl or benzyl esters are preferred within the sense of the present invention:

Preferred compounds (PC):
1) 2-Phosphono-2-methyl-3-butyl-succinic acid
2) 2-Phosphono-3-butyl-succinic acid, m.p. 157°–9° C. (decomp.)
3) 2-Phosphono-3-pentyl-succinic acid
4) 2-Phosphono-3-(3-methyl-1-butyl)-succinic acid, m.p. 151°–2° C. (decomp.)
5) 2-Phosphono-3-methyl-3-butyl-succinic acid
6) 2-Phosphono-3-(2-propen-1-yl)-succinic acid
7) 2-Phosphono-3-(2-methyl-2-propen-1-yl)-succinic acid
8) 2-Phosphono-3-cyclohexyl-succinic acid
9) 2-Phosphono-3-(2-cyclohexen-1-yl)-succinic acid
10) 2-Phosphono-3-(phenylmethyl)-succinic acid, sodium salt: $^1$H-NMR (D$_2$O): 3.35 (dd, 1H), 3.25–3.0 (m, 3H), 2.92–2.80 (m, 1H); $^{31}$P-NMR (D$_2$O): 18.01 (s), 16.99 (s)
11) 2-Phosphono-3-(4-hydroxycyclohexyl)-succinic acid
12) 2-Phosphono-3-(4-aminocyclohexyl)-succinic acid
13) 2-Phosphono-3-(4-dimethylaminocyclohexyl)-succinic acid
14) 2-Phosphono-3-(4-hydroxy-cyclohex-2-en-1-yl)-succinic acid
15) 2-Phosphono-3-(2-hydroxycyclopentyl)-succinic acid
16) 2-Phosphono-3-(4-isopropylcyclohexyl)-succinic acid
17) 2-Phosphono-3-cycloheptyl-succinic acid
18) 2-Phosphono-3-(2-phenylethyl)-succinic acid
19) 2-Phosphono-3-(3-phenylpropyl)-succinic acid
20) 2-Phosphono-3-(4-methoxyphenylmethyl)-succinic acid
21) 2-Phosphono-3-(4-hydroxyphenylmethyl)-succinic acid
22) 2-Phosphono-3-(4-dimethylaminophenylmethyl)-succinic acid
23) 2-Phosphono-3-(4-aminophenylmethyl)-succinic acid
24) 2-Phosphono-3-(4-methylphenylmethyl)-succinic acid
25) 2-Phosphono-3-(3-chlorophenylmethyl)-succinic acid
26) 2-Phosphono-3-(2-methoxyphenylmethyl)-succinic acid
27) 2-Phosphono-3-(4-aminocarbonylphenylmethyl)-succinic acid
28) 2-Phosphono-3-(4-amidinophenylmethyl)-succinic acid
29) 2-Phosphono-3-(4-cyanophenylmethyl)-succinic acid
30) 2-Phosphono-3-(3,4-dimethoxyphenylmethyl)-succinic acid
31) 2-Phosphono-3-(2-(3,4-dimethoxyphenyl)-ethyl)-succinic acid
32) 2-Phosphono-3-(2-(4-aminophenyl)ethyl)-succinic acid
33) 2-Phosphono-3-(1-naphthyl)-succinic acid
34) 2-Phosphono-3-(2-naphthyl)-succinic acid, m.p. 180°–2° C. (decomp.)
35) 2-Phosphono-3-(4-phenylphenyl)-succinic acid
36) 2-Phosphono-3-(4-(4-amidinophenyl)phenyl)-succinic acid
37) 2-Phosphono-2-amino-3-methyl-succinic acid
38) 2-Phosphono-2-hydroxy-3-methyl-succinic acid
39) 2-Phosphono-3-amino-3-methyl-succinic acid
40) 2-Phosphono-3-hydroxy-3-methyl-succinic acid
41) 2-Phosphono-2-amino-3-ethyl-succinic acid
42) 2-Phosphono-2-methoxy-3-ethyl-succinic acid
43) 2-Phosphono-3-amino-3-ethyl-succinic acid
44) 2-Phosphono-3-methoxy-3-ethyl-succinic acid
45) 2-Phosphono-2-amino-3-phenyl-succinic acid
46) 2-Phosphono-3-amino-3-phenyl-succinic acid
47) 2-Phosphono-2-methoxy-3-phenyl-succinic acid
48) 2-Phosphono-2-amino-3-phenylmethyl-succinic acid
49) 2-Phosphono-3-methoxy-3-phenylmethyl-succinic acid
50) 2,3-Dimethoxy-2-phosphono-succinic acid
51) 2-Phosphono-2-methoxy-3-(4-phenyl)phenyl-succinic acid
52) 2-Phosphono-3-(2-cyclohexyl)ethyl-succinic acid
53) 2-Phosphono-3-ethyloxy-succinic acid
54) 2-Phosphono-3-butyloxy-succinic acid
55) 2-Phosphono-3-cyclohexyloxy-succinic acid
56) 2-Phosphono-3-phenyloxy-succinic acid
57) 2-Phosphono-3-(4-hydroxyphenyloxy)-succinic acid
58) 2-Phosphono-3-(4-dimethylaminophenyloxy)-succinic acid
59) 2-Phosphono-3-(1-naphthyloxy)-succinic acid
60) 2-Phosphono-3-(4-(1-pyrrolidinopropyl)phenyloxy)-succinic acid
61) 2-Phosphono-3-(4-(1-pyrrolidinopropyl-oxy)phenyloxy)-succinic acid
62) 2-Phosphono-3-(4-phenyl)phenyloxy)-succinic acid
63) 2-Phosphono-3-(4-(4-amidinophenyl)phenyloxy)-succinic acid 64) 2-Phosphono-3-hydroxymethyl-succinic acid
65) 2-Phosphono-3-methoxymethyl-succinic acid
66) 2-Phosphono-3-propoxymethyl-succinic acid
67) 2-Phosphono-3-cyclohexyloxymethyl-succinic acid
68) 2-Phosphono-3-phenoxymethyl-succinic acid
69) 2-Phosphono-3-(4-hydroxyphenyl)oxymethyl-succinic acid
70) 2-Phosphono-3-(4-dimethylaminophenyl)oxymethyl-succinic acid
71) 2-Phosphono-3-(1-naphthyloxymethyl)-succinic acid
72) 2-Phosphono-3-(4-(phenyl) phenyl) oxymethyl-succinic acid
73) 2-Phosphono-3-(2-hydroxyethyl)-succinic acid
74) 2-Phosphono-3-(3-methoxypropyl)-succinic acid
75) 2-Phosphono-3-(3-phenoxypropyl)-succinic acid
76) 2-Phosphono-3-(4-(4-methoxyphenylmethyloxy)butyl-succinic acid
77) 2-Phosphono-3-methylthio-succinic acid
78) 2-Phosphono-3-propylthio-succinic acid, m.p. 154°–5° C.
79) 2-Phosphono-3-propyl-thiomethyl-succinic acid, m.p. 80° C. (decomp.)
80) 2-Phosphono-3-phenylthio-succinic acid, m.p. 149°–50° C.
81) 2-Phosphono-3-methylthiomethyl-succinic acid
82) 2-Phosphono-3-ethylthio-succinic acid, m.p. 160°–2° C.
83) 2-Phosphono-3-ethylthiomethyl-succinic acid, m.p. 176°–7° C.
84) 2-Phosphono-3-phenylthiomethyl-succinic acid, m.p. 171°–2° C.
85) 2-Phosphono-3-(4-(4-methoxyphenyl)thiobutyl-succinic acid
86) 2-Phosphono-3-(2-piperidino)-succinic acid
87) 2-Phosphono-3-(2-tetrahydropyranyl)-succinic acid
88) 2-Phosphono-3-(2-(4-methoxy)piperidino)-succinic acid
89) 2-Phosphono-3-(3-phenoxyethyl)-succinic acid, sodium salt: $^1$H-NMR (D$_2$O): 7.40 (dd, 2H), 7.05 (m, 3H), 4.20 (m, 2H), 3.50–3.15 (m, 2H), 2.65 (m, 1H), 2.22 (m, 1H); $^{31}$P-NMR (D$_2$O): 15.17 (s), 14.53 (s)
90) 2-Phosphono-3-((2-piperidino)methyl)-succinic acid,
91) 2-Phosphono-3-((2-tetrahydropyranyl)methyl)-succinic acid
92) 2-Phosphono-3-(2-(2-piperidino) ethyl)-succinic acid
93) 2-Phosphono-3-(2-pyrrolidino)-succinic acid
94) 2-Phosphono-3-(2-(4-hydroxy)pyrrolidino)-succinic acid
95) 2-Phosphono-3-(2-tetrahydrofuranyl)-succinic acid
96) 2-Phosphono-3-(2-tetrahydrothiophenyl)-succinic acid
97) 2-Phosphono-3-((2-tetrahydrofuranyl)methyl)-succinic acid
98) 2-Phosphono-3-((2-tetrahydrothiophenyl)methyl)-succinic acid
99) 2-Phosphono-3-((2-pyrrolidino)methyl)-succinic acid
100) 2-Phosphono-3-(3-(2-pyrrolidino)propyl)-succinic acid
101) 1-Phosphono-1,2-cyclohexane-dicarboxylic acid
102) 1-Phosphono-1,2-cyclopentane-dicarboxylic acid
103) 3-Phosphono-2,3-piperidine-dicarboxylic acid
104) 3-Phosphono-2,3-pyrrolidine-carboxylic acid
105) 3-Phosphono-2,3-tetrahydropyrane-dicarboxylic acid
106) 3-Phosphono-2,3-tetrahydrofuran-dicarboxylic acid
107) 2-Phosphono-2,3-morpholine-dicarboxylic acid
108) 2-Phosphono- 3-(4-hydroxyphenylmethyl)-succinic acid: $^1$H-NMR (D$_2$O): 7.26 (d, 1H), 7.22 (d, 1H), 6.90 (d, 2H), 3.12–2.98 (m, 2H), 2.93–2.80 (m, 2H) $^{31}$P-NMR (D$_2$O): 17.82 (s), 15.93 (s)

The following examples show some variants of processes which can be used to synthesize the compounds according to the invention. However, they are not intended to represent a limitation of the subject matter of the invention. The structure of compounds was confirmed by $^1$H-, $^{31}$P- and if necessary by $^{13}$C-NMR spectroscopy. Purity of the substances was determined by means of C, H, N, P and if necessary Na analysis as well as by thin layer chromatography or thin layer electrophoresis (cellulose, oxalate buffer of pH=4.0).

EXAMPLE 1

2-Phospono-3-cyclohexylmethyl-succinic acid a) 8.2 ml (160 mmol) bromine is added dropwise within 2 hours to a mixture of 6.8 ml (40 mmol) 3-cyclohexylpropionic acid and 0.8 g (26 mmol) red phosphorus in 40 ml carbon tetrachloride which was heated to 80° C. Afterwards the reaction mixture is heated for a further 15 hours under reflux, then it is cooled and the solvent is removed on a rotary evaporator. The remaining residue is admixed with 50 ml ethanol while cooling on ice and the solution obtained is heated for one hour under reflux. Subsequently the reaction solution is evaporated to dryness, the residue is taken up in 30 ml saturated sodium bicarbonate solution and the aqueous solution obtained in this way is extracted three times with 50 ml ether each time. The combined ether phases are shaken with 10 ml saturated sodium thiosulfate solution and dried over sodium sulfate. After removing the ether, 10 g 2-bromo-2-cyclohexylpropionic acid ethyl ester is obtained as a yellow oil. $^1$H-NMR (CDCl$_3$): δ=4.33 ppm (t, 1H); 4.16 (q, 2H); 1.85 (t, 2H); 1.73–1.28 (m, 6H); 1.23 (t, 3H); 1.22–0.74 (m, 5H).

b) A solution of 4 ml (20 mmol) phosphonoacetic acid triethyl ester in 30 ml absolute dimethylformamide (abs. DMF) is admixed with 0.48 g (20 mmol) sodium hydride at room temperature and stirred until the formation of hydrogen is completed (30 min). 5.26 g (20 mmol) of the 2-bromo-3-cyclohexyl-propionic acid ethyl ester in 20 absolute DMF prepared above is added dropwise to this solution and the reaction mixture is subsequently stirred for 8 hours at room temperature. Afterwards DMF is removed on a rotary evaporator, the residue is taken up in 20 ml saturated ammonium chloride solution and the aqueous solution obtained is extracted three times with 50 ml ethyl acetate each time. After drying the combined organic phases over sodium sulfate and removing the solvent, the crude product is purified by means of column chromatography on silica gel (mobile solvent:ethyl acetate/isohexane=2/1). 3.5 g 2-phosphono-3-cyclohexylmethyl-succinic acid tetraethyl ester is obtained as a colourless oil. $^1$H-NMR (CDCl$_3$): δ=4 ppm (m, 8H); 3.26 (q, 1H); 3.15–2.97 (m, 1H); 1.99–1.4 (m, 6H); 1.33–1.0 (m, 17H); 0.97–0.68 (m, 2H); (the product is present as a diastereomeric mixture in a ratio of 1:1). $^{31}$P-NMR (CDCl$_3$): δ=19.88 ppm; δ=18.61 ppm.

c) 2.5 g (6.2 mmol) 2-phosphono-3-cyclohexylmethyl-succinic acid tetraethyl ester is suspended in 50 ml 6N hydrochloric acid. The suspension is then heated for 24 hours under reflux and subsequently the cooled aqueous solution is shaken twice with 50 ml ethyl acetate each time. After evaporating the aqueous phase, 1.3 g 2-phosphono-3-cyclohexylmethyl-succinic acid is obtained. This is dissolved in 10 ml water and the acidic solution obtained in this way is adjusted to pH 7 (pH electrode) with 1N sodium hydroxide solution. After removing the water, the residue is suspended in diethyl ether and the suspension is filtered. 1.2 g 2-phosphono- 3-cyclohexyl-methyl-succinic acid trisodium salt is obtained in this way. m.p. >250° C. C,H analysis $C_{11}H_{16}Na_3O_7P \times 2.5\ H_2O$ calc. C 32.60, H 5.22; found C 32.63, H 5.25. 2-Phosphono-3-phenylmethyl-succinic acid was prepared analogously to example 1 starting with 3-phenylpropionic acid. The compound is present as a diastereomeric mixture in a ratio of 1/1. $^1$H-NMR ($D_2O$); δ=7.4 ppm (m, 5H); 3.5–2.85 (m, 2H); $^{31}$P-NMR ($D_2O$): δ=15.25 ppm (s).

EXAMPLE 2

2-Phosphono-3-(3,4-dimethoxyphenyl)methyl-succinic acid a) 85.68 ml 1.6N butyllithium solution in hexane (0.136 mol) was admixed with 19.27 ml (0.136 mol) diisopropylamine at −10° C. under nitrogen. Afterwards the white suspension was stirred for 30 minutes at −10° C., admixed with 200 ml absolute tetrahydrofuran (abs. THF) and the lithium diisopropylamide solution obtained was cooled to −78° C. Subsequently a solution of 25.6 ml (0.2 mol) freshly distilled chlorotrimethylsilane in 20 ml abs. THF was quickly added, a solution of 24.5 g (0.109 mol) 3-(3,4-dimethoxyphenyl)-propionic acid methyl ester in 50 ml abs. THF was then added dropwise within 10 minutes and afterwards the reaction mixture was stirred for one hour at −78° C. Subsequently 22.6 g (0.127 mol) N-bromosuccinimide was added, the reaction mixture was allowed to reach room temperature (1 h) and it was stirred for a further 8 hours. After removing the precipitate that formed by filtration, the mother liquor was concentrated in a vacuum, the residue was taken up in 100 ml diethyl ether, the ether solution was washed with saturated sodium thiosulfate solution and dried over sodium sulfate. After removing the ether, 33.8 g 2-bromo-3-(3,4-dimethoxyphenyl)-propionic acid methyl ester was obtained as a light brown oil. $^1$H-NMR ($CDCl_3$): δ=6.75 (m, 3H); 4.35 (dd, 1H); 3.85 (s, 3H); 3.83 (s, 3H); 3.7 (s, 3H); 3.4 (dd, 1H); 3.15 (dd, 1H).

b) Alkylation of phosphonoacetic acid triethyl ester with 2-bromo-3-(3,4-dimethoxyphenyl)-propionic acid methyl ester which was carried out analogously to example 1b) yielded 2-diethylphosphono-3-(3,4-dimethoxyphenyl) methyl-succinic acid methyl-ethyl ester. This is present as a diastereomeric mixture in a ratio of 1/2. $^1$H-NMR ($CDCl_3$): δ=6.73 ppm (d, 1H); 6.68 (s, 1H); 6.67 (d, 1H); 4.14 (m, 6H); 3.78 (two s, 2×3H); 3.47 (s, 3H); 3.39–3.18 (m, 3H); 2.97–2.70 (m, 1H); 1.22 (m, 9H); $^{31}$P-NMR ($CDCl_3$): δ=18.34 ppm (S); δ=18.17 ppm (s).

c) The ester groups in 2-diethyl-phosphono-3-(3,4-dimethoxy-phenyl)methyl succinic acid methyldiethyl ester are saponified analogously to example 1c) and yielded free 2-phosphono-3-(3,4-dimethoxyphenyl)-methyl succinic acid, m.p. 195° C. (decomp.).

EXAMPLE 3

2-Phosphono-3-(4-hydroxybutyl)-succinic acid a) A mixture of 10.6 ml (0.1 mol) ε-caprolactone and 1.97 g (0.015 mol) potassium carbonate in 50 ml methanol is stirred for one hour at room temperature, then the potassium carbonate is removed by filtration and the mother liquor is evaporated to dryness in a vacuum. The residue is taken up in 20 ml saturated ammonium chloride solution and the solution is extracted three times with 50 ml diethyl ether each time. After drying the combined organic phases over sodium sulfate and removing the solvent, 12.2 g 6-hydroxycaproic acid methyl ester is obtained which is reacted further without additional purification.

b) A solution of 5.8 g (40 mmol) 6-hydroxycaproic acid methyl ester and 8.2 g (120 mmol) imidazole in 50 ml dry dimethylformamide (DMF) was admixed with 6.8 g (45 mmol) tert.-butyldimethylsilyl chloride. Subsequently the reaction mixture was allowed to stir for 4 hours at room temperature, the DMF was removed in a vacuum, the residue was taken up in 500 ml water and the aqueous solution was shaken three times with 100 ml diethyl ether each time. After drying the combined ether phases over sodium sulfate and removing the solvent, the crude product was purified by column chromatography on silica gel. (Mobile solvent:ethyl acetate/isohexane=1/10). 4.1 g 6-tert.-butyl-dimethylsilyloxycaproic acid methyl ester was obtained in this way. $^1$H-NMR ($CDCl_3$): δ=3.61 ppm (s, 3H); 3.55 (t, 2H); 2.26 (t, 2H); 1.60 (m, 2H); 1.49 (m, 2H); 1.30 (m, 2H); 0.85 (s, 9H); 0.001 (s, 6H).

c) Low-temperature bromination of 6-tert.-butyl-dimethyl-silyloxycaproic acid methyl ester which was carried out analogously to example 2a), yielded 2-bromo-6-tert.-butyldimethylsilyloxycaproic acid methyl ester. $^1$H-NMR ($CDCl_3$): δ=4.19 ppm (dd, 1H); 3.70 (s, 3H); 3.52 (t, 2H); 2.0 (m, 2H); 1.52–1.40 (m, 4H); 0.83 (s, 9H); 0,001 (s, 6H)

d) Alkylation of phosphonoacetic acid triethyl ester with 2-bromo-6-tert.-butyldimethylsilyloxy-caproic acid methyl ester which was carried out analogously to example 1b) yielded 2-phosphono-3-(4-tert.-butyldimethylsilyloxybutyl)-succinic acid methyltriethyl ester as a light yellow oil. $^1$H-NMR (DMSO-$d^6$) (diastereomeric mixture 1/1): 4.05 (m, 6H); 3.55 (s, 3H); 3.50 (m, 2H); 3.15 (m, 1H); 2.85 (m, 1H); 1.40 (m, 2H); 1.15 (m, 4H+9H); 0.85 (s, 9H); 0.001 (s, 6H); $^{31}$P-NMR (DMSO-$d^6$): δ=24.79 ppm (s): δ=24.18 ppm (s).

e) A solution of 1.4 g (2.9 mmol) 2-phosphono-3-(4-tert.-butyldimethylsilyloxybutyl)-succinic acid methyl triethyl ester in 5 ml acetonitrile is admixed with 3 ml 2 percent (in acetonitrile) aqueous hydrofluoric acid. Subsequently the reaction mixture is stirred for 2 hours at room temperature, afterwards the solvent is removed in a vacuum, the residue is taken up in 10 ml saturated sodium bicarbonate solution and the aqueous solution is extracted three times with 20 ml ethyl acetate each time. After drying the combined organic phases over sodium sulfate and removing the solvent, 0.6 g 2-phosphono-3-(4-hydroxybutyl)-succinic acid methyl-triethyl ester is obtained as a colourless viscous oil. $^1$H-NMR ($CDCl_3$) (diastereomeric mixture 1/1): δ=4.05 ppm (m, 6H); 3.60 (s, 3H); 3.55 (m, 2H); 3.31 (m, 1H); 3.20 (m, 1H); 1.85 (m, 1H); 1.65–1.32 (m, 5H); 1.22 (m, 9H); $^{31}$P-NMR ($CDCl_3$): δ=20.05 ppm (s): δ=19.90 ppm (s).

f) The ester groups in 2-phosphono-3-(4-hydroxybutyl)-succinic acid methyl-triethyl ester were saponified analogously to example 1c) and yielded free 2-phosphono-3-(4-hydroxybutyl)-succinic acid which was converted into the tetrasodium salt using 1N NaOH. C,H analysis: $C_8H_{11}O_8PNa_4 \times 2.5\ H_2O$ (MW=403) calc. C 23.82; H 3.97; P 7.69; found C 23.75; H 3.90; P 7.69.

EXAMPLE 4

2-Phosphono-3-(3-hydroxypropyl)-succinic acid a) 5-Hydroxyvaleric acid methyl ester was prepared analogously to example 3a) from δ-valerolactone which was reacted further without additional purification.

b) The silyl protecting group for the hydroxyl group was introduced into 5-hydroxyvaleric acid methyl ester analogously to example 3b) and yielded 5-tert.-butyldimethylsilyloxyvaleric acid methyl ester as a light yellow oil. $^1$H-NMR (CDCl$_3$): δ=3.67 ppm (s, 3H); 3.54 (t, 2H); 1.95 (t, 2H); 1.57 (m, 2H); 1.48 (m, 2H); 0.82 (s, 9H); 0.01 (s, 6H);

c) Low-temperature bromination of 5-tert.-butyldimethylsilyloxyvaleric acid methyl ester which was carried out analogously to example 2a), yielded 2-bromo-5-tert.-butyldimethylsilyloxyvaleric acid methyl ester as a yellow oil. $^1$H-NMR (DMSO-d$^6$): δ=4.5 ppm (dd, 1H); 3.67 (s, 3H); 3.54 (t, 2H); 1.95 (m, 2H); 1.48 (m, 2H); 0.80 (s, 9H); 0.01 (s, 6H).

d) Alkylation of phosphonoacetic acid triethyl ester with 2-bromo-5-tert.-butyldimethylsilyloxyvaleric acid methyl ester, which was carried out analogously to example 1b), yielded 2-phosphono-3-(3-tert.-butyldimethylsilyloxypropyl)-succinic acid methyl-triethyl ester as a colourless yellow oil. $^1$H-NMR (DMSO-d$^6$) (diastereomeric mixture 1/1): δ=4.0 ppm (m, 6H); 3.58 (s, 3H); 3.47 (m, 2H); 3.17 (m, 1H); 2.83 (m, 1H); 1.38 (m, 2H); 1.13 (m, 2H+9H); 0.81 (s, 9H); 0.01 (s, 6H); $^{31}$P-NMR (DMSO-d$^6$): δ=24.72 ppm (s): δ=24.21 ppm (s).

The silyl protecting group was removed from 2-phosphono-3-(3-tert.-butyldimethylsilyloxypropyl) succinic acid methyl-triethyl ester analogously to example 3e) and yielded 2-phosphono-3-(3-hydroxypropyl)-succinic acid methyl-triethyl ester. $^1$H-NMR (DMSO-d$^6$) (diastereomeric mixture 1/1): δ=4.38 ppm (t, 1H; OH); 4.05 (m, 6H); 3.5 (s, 3H); 3.30 (m, 2H); 3.15 (m, 1H); 3.0 (m, 1H); 1.62–1.20 (m, 4H); 1.17 (m, 9H).

f) The ester groups in 2-phosphono-3-(3-hydroxypropyl) -succinic acid methyl-triethyl ester were hydrolyzed analogously to example 1c) and yielded free 2-phosphono-(3-hydroxypropyl)-succinic acid which was converted into the trisodium salt with 1N NaOH. C,H analysis: C$_7$H$_{10}$O$_8$Na$_3$P× 0.5 H$_2$O (331) calc. C 25.39; H 3.75; P 9.37; found C 25.27; H 3.51; P 9.60.

EXAMPLE 5 a) 7.19 g (30 mmol) 2-bromomethylfumaric acid methyl ester (J. Org. Chem. 34, 1228 (1969) is added to a solution of 33 mmol sodium in 100 ml methanol and heated for 12 hours under reflux. The methanol is removed by distillation and the residue is purified on silica gel (mobile solvent diethyl ether/heptane 1:4). 2.82 g 3-methoxymethylfumaric acid dimethyl ester is obtained in this way.

b) 900 mg (5 mmol) 3-methoxymethylfumaric acid dimethyl ester is added to a solution of 5 mmol NaH in toluene and 0.55 g (5 mmol) phosphorous acid dimethyl ester is slowly added dropwise. After 1 hour at room temperature it is concentrated by evaporation and the mixture is purified by chromatography on silica gel (mobile solvent acetone/toluene 1:1). Yield 0.9 g (60%) colourless oil. 800 mg (2.5 mmol) 3-methoxymethyl-2-diethylphosphono-succinic acid dimethyl ester is heated in 70 ml 6N HCl for 6 hours at 140° C. The solution is concentrated by evaporation and the residue is precipitated from water/acetone. 540 mg (79%) of an amorphous, white powder is obtained, the structure of which was confirmed by NMR and mass spectroscopy. f.p. 144° C. (decomp.).

EXAMPLE 6

1-Phosphono-1,2-cyclohexane-dicarboxylic acid a) A solution of 1.2 g (3.3 mmol) of the 2-phosphono-3-(4-hydroxybutyl)-succinic acid ester prepared according to example 3e) and 0.73 ml (5.0 mmol) triethylamine in 20 ml diethyl ether is admixed dropwise at room temperature with 0.3 ml (3.9 mmol) methanesulfonic acid chloride in 5 ml diethyl ether and subsequently the reaction mixture is stirred for 30 minutes. Afterwards the precipitated precipitate is removed by filtration, the ether solution is washed in succession with 10 ml dilute hydrochloric acid, 20 ml saturated sodium bicarbonate solution and 20 ml water and dried over sodium sulfate. After removing the solvent, 1.2 g 2-phosphono-3-(4-methane-sulfonyloxy-butyl)-succinic acid methyl-triethyl ester is obtained. $^1$H-NMR (CDCl$_3$): δ=4.1 ppm (m, 6H+2H); 3.65 (s, 3H); 3.48–3.03 (m, 2H); 2.92 (s, 3H); 1.85 (m, 2H); 1.78–1.40 (m, 4H); 1.22 (m, 9H).

b) 60 mg (2.5 mmol) sodium hydride is added to a solution of 1.1 g (2.5 mmol) 2-phosphono-3-(4-methanesulfonyloxybutyl)-succinic acid methyltriethyl ester in 50 ml dry dimethylformamide and the reaction mixture is then heated for 2 hours at 50° C. Subsequently the solvent is removed in a vacuum, the residue is taken up in 5 ml saturated ammonium chloride solution and the aqueous solution that is formed is extracted twice with 10 ml ethyl acetate each time. After drying the combined organic phases over sodium sulfate and removing the solvent, the crude product is purified by column chromatography on silica gel (mobile solvent:ethyl acetate). 520 mg 1-diethylphosphono-2-methoxycarbonyl-cyclohexane-carboxylic acid ethyl ester is obtained in this manner. $^1$H-NMR (CDCl$_3$) (mixture of diastereomers 1/3): δ=4.1 ppm (m, 6H); 3.60 (s, 3H); 3.40 (m, 1H); 2.11 (m, 2H); 1.86 (m, 2H); 1.61–135 (m, 4H); 1.22 (m, 9H). $^{31}$P-NMR (CDCl$_3$): δ=23.5 ppm (s); δ=22.97 ppm (s).

c) The ester groups in 1-diethylphosphono-2-methoxycarbonyl-cyclohexane-carboxylic acid ethyl ester were hydrolyzed analogously to example 1c) and yielded free 1-phosphono-1,2-cyclohexanedicarboxylic acid which was converted into the tetrasodium salt with 1N NaOH. $^1$H-NMR (D$_2$O): δ=2.80 ppm (m, 1H); 2.45 (m, 1H); 2.02 (m, 1H); 1.9–1.29 (m, 6H). $^{31}$P-NMR (D$_2$O): δ=18.05 ppm (s).

Experimental protocol

Inhibition of non-stimulated bone resorption by determining the [$^3$H]-tetracycline excretion in urine:

From birth rats are injected twice weekly with increasing amounts of a solution of 3.7×105 Bq/ml (10 μCi/ml) [7-$^3$H] -tetracycline ([$^3$H]TC; New England Nuclear, Boston, Mass.) having a specific activity of 679 mCi/mmol. The volume was increased per injection from 50 μl/week to 250 μl in the fifth week and was maintained for a further week. The total amount of administered [$^3$H]TC was 20 μCi per rat. 51 day old rats are rehoused in individual metabolic cages and receive a group feeding with feed containing 0.5% Ca and 0.35% P. This feed was prepared by addition of appropriate amounts of calcium gluconate and neutral sodium phosphate to feed having a low calcium and phosphate content (SODI 2134, Klingenthalmühle). During the entire course of the experiment the animals received distilled water ad libitum. After 10 days the collection of 24 hour urine was started. They received their feed daily at 11 o'clock. Urine was also collected at this time. The substances were administered daily in two subcutaneous injections (8 am and 5 pm). $^3$H-TC in the urine was determined by means of liquid scintillation by adding 10 ml of the scintillator Pico-Fluor 30 (Packard International, Zurich, Switzerland) to 1 ml urine.

| Compound | Examp. | Dosage | Resorp. Inhib |
|---|---|---|---|
| 2-phosphono-3-(4-hydroxy-butyl)-succinic acid | 3 | 2 × 100 mg/kg | 27% |
| 2-phosphono-3-(phenyl-methyl)-succinic acid | PC 10 | 2 × 200 mg/kg | 47% |
| 2-phosphono-3-(cyclohexyl-methyl)-succinic acid | 1 | 2 × 200 mg/kg | 64% |

We claim:
1. A compound of formula I,

wherein
R$^1$ and R$^2$ are each independently selected from the group consisting of hydrogen, lower alkyl groups, C$_3$–C$_7$ cycloalkyl groups and phenylmethyl groups,
R$^3$ and R$^4$ are each independently selected from the group consisting of hydrogen and lower alkyl groups, or, together with the carbon atoms to which they are bound, form a five- to seven- membered carbocyclic ring,
R$^5$ is selected from the group consisting of (1) C$_3$–C$_6$ alkenyl groups, (2) C$_3$–C$_7$ cycloalkyl groups, (3) phenylalkyl groups which are unsubstituted or have at least one substituent selected from the group consisting of C$_1$–C$_6$ alkyl groups, chlorine, bromine, fluorine, hydroxy groups, methoxy groups, benzyloxy groups, acetyloxy groups, carboxy groups, ethyoxcarbonyl groups, aminocarbonyl groups, methylaminocarbonyl groups, dimethylaminocarbonyl groups, cyano groups, amino groups, methylamino groups, dimethylamino groups, benzylamino groups, acetylamino groups, benzoylamino groups and amidino groups and (4) a group of formula a), R$^9$—X—alk—, wherein  a)

R$^9$ is selected from the group consisting of hydrogen, lower alkyl groups, C$_3$–C$_7$ cycloalkyl groups and phenyl groups which are unsubstituted or have at least one substituent selected from the group consisting of C$_1$–C$_6$ alkyl groups, chlorine, bromine, fluorine, hydroxy groups, methoxy groups, benzyloxy groups, acetyloxy groups, carboxy groups, ethoxycarbonyl groups, aminocarbonyl groups, methylaminocarbonyl groups, dimethylaminocarbonyl groups, cyano groups, amino groups, methylamino groups, dimethylamino groups, benzylamino groups, acetylamino groups, benzoylamino groups and amidino groups,
X is selected from the group consisting of a bond, oxygen and sulphur, and
alk is selected from the group consisting of a bond, a methylene chain, a saturated alkylene chain with 2–6 carbon atoms and an unsaturated alkylene chain with 2–6 carbon atoms,
and a pharmacologically acceptable salt thereof, an ester thereof or an optical isomer thereof,
with the proviso that where
R$^3$ is selected from the group consisting of hydrogen and C$_1$–C$_3$ alkyl groups and R$^4$ is hydrogen; R$^5$ is other than hydrogen, hydroxy groups, methoxy groups, C$_1$–C$_3$ alkyl groups and phenyl groups.

2. A compound as claimed in claim 1, wherein R$^3$ and R$^4$, together with the carbon atoms to which they are bound, form a carbocyclic ring selected from the group consisting of cyclopentyl, cyclohexyl, cycloheptyl, cyclopentenyl and cyclohexenyl.

3. A compound as claimed in claim 1, wherein said C$_3$–C$_7$ cycloalkyl groups of R$^1$, R$^2$, R$^5$ and R$^9$ are selected from the group consisting of cyclopropyl, cyclopentyl and cyclohexyl.

4. A compound as claimed in claim 1, wherein said phenylalkyl groups of R$^5$ are selected from the group consisting of benzyl, phenethyl, phenylpropyl, phenylbutyl and phenylpentyl.

5. A compound as claimed in claim 4, wherein said phenylalkyl groups of R$^5$ are selected from the group consisting of benzyl, phenethyl and phenylpentyl.

6. A compound as claimed in claim 1, wherein said alk group is selected from the group consisting of methylene, ethylene, propylene, butylene, 2-methyl-propylene, pentylene, hexylene and 2-butenylene.

7. A compound as claimed in claim 1, wherein the pharmacologically acceptable salt is selected from the group consisting of monoalkali salt, dialkali salt and ammonium salt.

8. A compound as claimed in claim 1, wherein the pharmacologically acceptable salt is selected form the group consisting of sodium salt and potassium salt.

9. A compound as claimed in claim 1, wherein the compound is present as a pure enantiomer.

10. A pharmaceutical composition suitable for the treatment of a calcium metabolism disorder comprising the compound of claim 1 and a pharmaceutically acceptable carrier.

11. A pharmaceutical composition as claimed in claim 10 wherein the pharmaceutically acceptable carrier is a liquid carrier.

12. A composition as claimed in claim 11, wherein the liquid carrier is dispensed into ampoules.

13. A composition as claimed in claim 10, wherein the pharmaceutically acceptable carrier is a solid carrier.

14. A compound as claimed in claim 1, wherein the compound is selected from the group consisting of
1) 2-Phosphono-2-methyl-3-butyl-succinic acid
2) 2-Phosphono-3-butyl-succinic acid
3) 2-Phosphono-3-pentyl-succinic acid
4) 2-Phosphono-3-(3-methyl-1-butyl)-succinic acid
5) 2-Phosphono-3-methyl-3-butyl-succinic acid
6) 2-Phosphono-3-(2-propen-1-yl)-succinic acid
7) 2-Phosphono-3-(2-methyl-2-propen-1-yl)-succinic acid
8) 2-Phosphono-3-cyclohexyl-succinic acid
9) 2-Phosphono-3-(phenylmethyl)-succinic acid
10) 2-Phosphono-3-cycloheptyl-succinic acid
11) 2-Phosphono-3-(2-phenylethyl)-succinic acid
12) 2-Phosphono-3-(3-phenylpropyl)-succinic acid
13) 2-Phosphono-3-(4-methoxyphenylmethyl)-succinic acid
14) 2-Phosphono-3-(4-hydroxyphenylmethyl)-succinic acid
15) 2-Phosphono-3-(4-dimethylaminophenylmethyl)-succinic acid 16) 2-Phosphono-3-(4-aminophenylmethyl)-succinic acid
17) 2-Phosphono-3-(4-methylphenylmethyl)-succinic acid
18) 2-Phosphono-3-(3-chlorophenylmethyl)-succinic acid
19) 2-Phosphono-3-(2-methoxyphenylmethyl)-succinic acid
20) 2-Phosphono-3-(4-aminocarbonylphenylmethyl)-succinic acid
21) 2-Phosphono-3-(4-amidinophenylmethyl)-succinic acid
22) 2-Phosphono-3-(4-cyanophenylmethyl)-succinic acid
23) 2-Phosphono-3-(3,4-dimethoxyphenylmethyl)-succinic acid
24) 2-Phosphono-3-(2-(3,4-dimethoxyphenyl)-ethyl)-succinic acid
25) 2-Phosphono-3-(2-(4-aminophenyl)ethyl)-succinic acid
26) 2-Phosphono-3-methoxy-3-ethyl-succinic acid
27) 2-Phosphono-3-methoxy-3-phenylmethyl-succinic acid
28) 2-Phosphono-3-(2-cyclohexyl)ethyl-succinic acid
29) 2-Phosphono-3-ethyloxy-succinic acid
30) 2-Phosphono-3-butyloxy-succinic acid
31) 2-Phosphono-3-cyclohexyloxy-succinic acid
32) 2-Phosphono-3-phenyloxy-succinic acid
33) 2-Phosphono-3-(4-hydroxyphenyloxy)-succinic acid
34) 2-Phosphono-3-(4-dimethylaminophenyloxy)-succinic acid
35) 2-Phosphono-3-hydroxymethyl-succinic acid
36) 2-Phosphono-3-methoxymethyl-succinic acid
37) 2-Phosphono-3-propoxymethyl-succinic acid
38) 2-Phosphono-3-cyclohexyloxymethyl-succinic acid
39) 2-Phosphono-3-phenoxymethyl-succinic acid
40) 2-Phosphono-3-(4-hydroxyphenyl)oxymethyl-succinic acid
41) 2-Phosphono-3-(4-dimethylaminophenyl)oxymethyl-succinic acid
42) 2-Phosphono-3-(2-hydroxyethyl)-succinic acid
43) 2-Phosphono-3-(3-methoxypropyl)-succinic acid
44) 2-Phosphono-3-(3-phenoxypropyl)-succinic acid
45) 2-Phosphono-3-(4-(4-methoxyphenylmethyloxy)butyl)-succinic acid
46) 2-Phosphono-3-methylthio-succinic acid
47) 2-Phosphono-3-propylthio-succinic acid
48) 2-Phosphono-3-propyl-thiomethyl-succinic acid
49) 2-Phosphono-3-phenylthio-succinic acid
50) 2-Phosphono-3-methylthiomethyl-succinic acid
51) 2-Phosphono-3-ethylthio-succinic acid
52) 2-Phosphono-3-ethylthiomethyl-succinic acid
53) 2-Phosphono-3-phenylthiomethyl-succinic acid
54) 2-Phosphono-3-(3-phenoxyethyl)-succinic acid
55) 1-Phosphono-1,2-cyclohexane-dicarboxylic acid
56) 1-Phosphono-1,2-cyclopentane-dicarboxylic acid
57) 2-Phosphono-3-(4-hydroxyphenylmethyl)-succinic acid
58) 2-Phosphono-3-(4-(4-methoxylphenyl)thiobutyl)-succinic acid
59) 2-Phosphono-3-cyclohexylmethyl-succinic acid
60) 2-Phosphono-3-(4-hydroxybutyl)-succinic acid and
61) 2-Phosphono-3-(3-hydroxypropyl)-succinic acid.

15. A method of treating a calcium metabolism disorder in a patient in need of such treatment, comprising administering to the patient a calcium-metabolism-disorder-treating effective amount of the compound of claim 1.

16. A method as claimed in claim 15, wherein the compound is administered enterally.

17. A method as claimed in claim 15, wherein the compound is administered parenterally.

18. A method as claimed in claim 15, wherein the compound is administered at a daily dose of about 10–1000 mg.

19. A method as claimed in claim 18, wherein the compound is administered at a daily dose of about 100–500 mg.

20. A method as claimed in claim 18, wherein the daily dose is divided into a plurality of individual doses.

* * * * *